(12) United States Patent
Bosbach et al.

(10) Patent No.: US 9,176,044 B2
(45) Date of Patent: Nov. 3, 2015

(54) DEVICE AND METHOD FOR DETECTING DEPOSITS

(75) Inventors: Franz Bosbach, Frankenthal (DE); Dieter Hanewald, Frankenthal (DE); Dieter-Heinz Hellmann, Kaiserslautern/Dansenberg (DE); Ulrich Stecker, Mannheim (DE); Sven Urschel, Eisenberg (DE)

(73) Assignee: KSB Aktiengesellschaft, Frankenthal (DE)

( * ) Notice: Subject to any disclaimer, the term of this patent is extended or adjusted under 35 U.S.C. 154(b) by 922 days.

(21) Appl. No.: 13/165,552

(22) Filed: Jun. 21, 2011

(65) Prior Publication Data
US 2011/0283780 A1  Nov. 24, 2011

Related U.S. Application Data

(63) Continuation of application No. PCT/EP2009/008815, filed on Dec. 10, 2009.

(30) Foreign Application Priority Data

Dec. 22, 2008 (DE) .................. 10 2008 064 038

(51) Int. Cl.
*G01N 25/72* (2006.01)
*G01N 17/00* (2006.01)
*G01N 25/18* (2006.01)

(52) U.S. Cl.
CPC .............. G01N 17/008 (2013.01); G01N 25/18 (2013.01)

(58) Field of Classification Search
CPC ..... G01K 1/143; G01N 25/72; G01N 17/008; G01N 2223/303; G01N 2223/6466

USPC ............ 374/4, 5, 7, 185, 29, 30, 141, 45, 57, 374/100, 101, 1, 10, 11, 31
See application file for complete search history.

(56) References Cited

U.S. PATENT DOCUMENTS

| | | | | |
|---|---|---|---|---|
| 4,036,051 A | * | 7/1977 | Fell et al. | 374/39 |
| 4,346,587 A | * | 8/1982 | Brindak | 73/61.62 |
| 4,383,438 A | * | 5/1983 | Eaton | 73/61.62 |
| 4,718,774 A | * | 1/1988 | Slough | 374/7 |
| 4,901,061 A | * | 2/1990 | Twerdochlib | 340/604 |
| 5,183,998 A | * | 2/1993 | Hoffman et al. | 219/492 |

(Continued)

FOREIGN PATENT DOCUMENTS

| | | |
|---|---|---|
| CN | 1504717 A | 6/2004 |
| DE | 10 2005 038 870 B3 | 3/2007 |

(Continued)

OTHER PUBLICATIONS

Translation of Chinese Search Report (one (1) page).
(Continued)

*Primary Examiner* — Gail Kaplan Verbitsky
(74) *Attorney, Agent, or Firm* — Crowell & Moring LLP

(57) ABSTRACT

A device and a method for detecting deposits (9) on walls (2) that are covered by a medium, in which as sensor (1) is integrated in the wall (2). A component (3) of the sensor (1) locally heats the medium in a region (4), and the temperature of the medium around the component (3) is detected. The sensor (1) relays temperature measurement signals to an analysis unit (8), where the degree of deposit formation is determined, e.g., by comparison with stored reference data.

20 Claims, 3 Drawing Sheets

(56) References Cited

U.S. PATENT DOCUMENTS

| | | | |
|---|---|---|---|
| 5,248,198 | A | 9/1993 | Droege |
| 6,023,969 | A * | 2/2000 | Feller .................. 73/204.25 |
| 6,328,467 | B1 | 12/2001 | Keyhani |
| 6,499,876 | B1 * | 12/2002 | Baginksi et al. .................. 374/7 |
| 6,834,515 | B2 | 12/2004 | Sunder et al. |
| 6,886,393 | B1 | 5/2005 | Romanet et al. |
| 7,581,874 | B2 * | 9/2009 | Hays et al. .................. 374/7 |
| 8,360,635 | B2 * | 1/2013 | Huang et al. .................. 374/147 |
| 8,431,615 | B2 * | 4/2013 | Chu et al. .................. 514/588 |
| 8,746,968 | B2 * | 6/2014 | Auret et al. .................. 374/45 |
| 2006/0108003 | A1 * | 5/2006 | Bradford et al. .................. 137/487.5 |
| 2008/0291965 | A1 * | 11/2008 | Wolferseder .................. 374/7 |
| 2009/0000764 | A1 | 1/2009 | Tochon et al. |
| 2012/0170610 | A1 * | 7/2012 | Ramos et al. .................. 374/5 |

FOREIGN PATENT DOCUMENTS

| | | |
|---|---|---|
| FR | 2 897 930 A1 | 8/2007 |
| WO | WO 00/43762 A1 | 7/2000 |
| WO | WO 02/04290 A1 | 1/2002 |
| WO | WO 2007/003801 A2 | 1/2007 |
| WO | WO 2009/135504 A1 | 11/2009 |

OTHER PUBLICATIONS

Corresponding English Translation of International Preliminary Report on Patentability (Forms PCT/IB/338 and PCT/IB/373) dated Jul. 7, 2011 with Form PCT/ISA/237 (eleven)(11) pages).
PCT/ISA/237 Form (Seven (7) pages).
International Search Report including English translation dated Mar. 10, 2010 (Six (6) pages).

* cited by examiner

DEVICE AND METHOD FOR DETECTING DEPOSITS

CROSS REFERENCE TO RELATED APPLICATIONS

This application is a continuation of international application no. PCT/EP2009/008815, filed Dec. 10, 2009, designating the United States of America, and published in German on Jul. 1, 2010 as WO 2010/072334, the entire disclosure of which is incorporated herein by reference. Priority is claimed based on Federal Republic of Germany patent application no. DE 10 2008 064 038.7, filed Dec. 22, 2008, the disclosure of which is likewise incorporated by reference herein.

BACKGROUND OF THE INVENTION

The invention relates to a device and a method for detecting deposits on walls which are covered by a medium.

The formation of deposits on the walls of installation parts is a serious economic and technical problem in many cases. For example, germs which impair the product quality may form in deposits. Deposits may also influence the flow characteristic in fittings. In the case of pipelines, deposits cause a rise in the pressure loss and may even result in blockages in the case of small internal diameters. The material from which the walls are produced may also be damaged, depending on the type of deposit.

The walls on which deposits form may be produced from different materials, for example stainless steel or plastic. The surface structure of the walls influences the formation of deposits. Rough surfaces provide a better surface for deposits than smooth surfaces. The walls on which deposits form may be flat or curved. Inner walls of fittings, pumps, pipelines or containers, in particular, are technically relevant.

The media with which the walls are covered and from which the deposits are deposited may be liquid or gaseous. It is also conceivable for paste-like substances to cover the walls. The invention is preferably used with liquids, the use of the invention being particularly suitable for aqueous solutions.

The deposits may be either inorganic or organic substances. Important examples of inorganic deposits are carbonates, oxides or hydroxides which are deposited on the walls of installation parts as scale, rust or a mineral deposit.

The most important organic deposits are biofilms. The formation of biofilms is a significant problem in the field of hygiene technology, for example the production of food, pharmaceuticals or biotechnology. Growth is caused by biomass and by impurities in the biomass. Bacteria, fungi, yeasts, diatoms and monads are only a few organisms which cause the build-up of biomass. If the biofouling caused by these organisms is not controlled, it can disrupt process operations and have an adverse effect on the product quality. When producing foods and pharmaceutical products, strict purity levels must be complied with. Contamination with bacteria or metabolites of microorganisms may damage health.

Many processes in hygiene technology are operated discontinuously as batch processes. The production process is interrupted at certain intervals of time, which are often based on empirical values, in order to clean deposits from the installation. The duration of the cleaning process is likewise often based on empirical values. In order to economically optimize the production processes, the production phases should be as long as possible and the cleaning phases should be as short as possible. However, no impairment in the product quality must be accepted in this case.

SUMMARY OF THE INVENTION

The object of the present invention is to provide a device and a method in which the formation of deposits on the inner walls of installation parts is continuously detected and quantitatively evaluated. The formation of deposits is intended to be detected and the degree of deposit formation determined. The use of the invention is intended to economically and ecologically optimize processes by virtue of the production times lasting as long as possible and the cleaning phases lasting only as long as necessary.

This object is achieved, according to the invention, by virtue of the fact that a sensor is integrated in the wall or is placed on the wall, a component of the sensor locally heating the medium in a region around this component, and the temperature of the medium and/or the temperature of the component being detected by the sensor, the sensor forwarding its signals to an evaluation unit which determines the degree of deposit formation by comparison with reference data.

The sensor according to the invention may be composed of a plurality of components which, in addition to pure measuring functions, also perform other tasks. The sensor is preferably in the form of a compact unit containing the individual components. In this manner, the sensor is easy to handle and can be integrated as a unit in the walls of fittings, pumps, pipelines or containers. In this case, it has proved to be favorable to provide the wall with a hole into which the sensor is inserted with an accurate fit. The sensor is preferably in the form of a cylindrical unit.

In one particularly advantageous embodiment of the invention, the sensor is inserted into the lateral inner surface of the wall in a flush manner. So that the surface of the sensor on the side of the medium can be a representative location for the formation of deposits, said surface may be produced from the same material as the walls of the corresponding installation part. It is also conceivable for the sensor to be intended to perform an early warning function for the formation of deposits. It is then favorable to form the surface of the sensor on the side of the medium from a material on which the deposits preferably form. For example, the surface of the sensor may be roughened or the sensor may be additionally coated with a net-like material. It may prove to be favorable to install the sensor at a poor point of the installation at which deposits preferably form.

In accordance with the invention, the sensor locally heats the medium. Heating is preferably effected in the immediate vicinity of the sensor surface on the side of the medium since the formation of deposits is intended to be detected directly at this location. If the sensor is inserted into the lateral inner surfaces of the wall in a flush manner, this location is locally representative of the formation of deposits on the walls.

The temperature established by heating at the local location of the medium is likewise detected by the sensor. The sensor forwards its data for the heating operation and the temperature measurement to an evaluation unit. The evaluation unit receives the signals from the sensor and converts them, if necessary, into standard signals. The evaluation unit also supplies the sensor with energy. It proves to be particularly favorable if the evaluation unit detects the current intensity with which the component of the sensor is heated. The signals which are forwarded by the sensor to the evaluation unit can also be digitized for further processing. Controllers or PCs may be used as evaluation units.

A comparison of the measurement data with reference data is decisive for determining the formation of deposits. Data relating to a sensor surface which is free of deposits are generally used as the reference. During the reference measurement, the process conditions preferably correspond to the conditions present when measuring the formation of deposits.

The degree of deposit formation may be specified, for example, using the height of the deposit layer which forms on the sensor. It is also conceivable for the structure of the deposit to change and become increasingly compact as the formation of the covering layer progresses. In this case, the physical variable would be the density of the deposit layer as a measure of the degree of deposit formation.

The signals from the sensor are evaluated, the degree of deposit formation being able to be determined using an algorithm. The data forwarded by the sensor to the evaluation unit are included in the algorithm as parameters. For example, the heating intensity with which the medium is heated, the temperature to which the medium is heated given a particular heating intensity, or the period needed to reach a temperature given a predefined heating intensity may be obtained as variables in the algorithm. The algorithm establishes a relationship between the sensor data and the degree of deposit formation. The individual parameters of the algorithm can be determined by means of regression calculation. In this case, the coefficients of the individual parameters of the algorithm are adjusted to match the measurement data. The aim is to simulate the test series as accurately as possible by means of mathematical functions. The coefficient of determination can be utilized for the quality of the adjustment.

It has proved to be expedient to use the period needed to reach a constant temperature level for the purpose of evaluation. In this variant, the heating intensity remains constant. When resistors are used as the heating component, this means that the component is always heated with the same current intensity regardless of whether the component is free of deposits or a deposit has formed. The period needed to set a temperature level with a deposit differs from the period needed to set a temperature level without a deposit. The evaluation unit can use this difference to determine the degree of deposit formation. In particular, the difference between the periods needed for cooling is suitable for drawing conclusions on the is formation of deposits.

In one particularly advantageous embodiment of the invention, the measurements for determining the formation of deposits are carried out with the same heating intensity as during the reference measurement. This means that the medium surrounding a component of the sensor is heated with the same heating intensity regardless of whether the sensor is free of deposits or a deposit has formed on the sensor. If a deposit has formed around this component, the deposit has an insulating effect. The temperature then increases in the heated region to a greater extent than if the component were not surrounded by a deposit. The difference from the reference measurement is particularly great when the medium flows around the component. In this case, the flow cannot cool the region around the component to such a great extent since the deposit has an insulating effect. If a resistor is used as the component, the current intensity flowing through the component can be used as a measure of the heating intensity. In this variant, the current intensity always remains the same, whether with or without a deposit. The evaluation unit can determine the degree of deposit formation using the difference between the temperature level established during a measurement with a deposit and that during a measurement without a deposit.

In another particularly advantageous embodiment of the invention, the temperature level to which the medium around the component is heated is kept constant. In this variant, the heating intensity needed to reach a particular temperature level is adjusted. When resistors are used as components, this means that only a lower current intensity is needed to reach the same temperature level when a deposit has formed around the component than when the component is free of deposits. The difference in the current intensity in comparison with the reference measurement is used as a measure of the degree of deposit formation.

In one particularly favorable variant of the invention, the medium around the component of the sensor is heated and the temperature in this region is detected using the same component. A temperature-dependent resistor is preferably used for this purpose. A voltage is applied to the resistor, with the result that a current flows through the resistor and heats the latter. If a deposit forms around the component, the temperature increases and the resistance of the component increases. As a result, the current intensity flowing through the component decreases. The decrease in the current intensity can be used as a measure of the degree of deposit formation.

In one particularly advantageous embodiment of the invention, the sensor additionally comprises a component which measures the temperature of the medium at a location which is not heated by the sensor. This makes it possible to compensate for measuring effects which are not based on deposit formation. In order to exclude these effects, the reference to the temperature measurement is always established with the second component. This prevents heating operations, which are caused by process-related operations, from corrupting the determination of deposit formation. A temperature-dependent resistor is preferably used as the additional component. If the temperature in the medium increases, the resistance increases. The increase in resistance can be determined by measuring the voltage or by measuring the current intensity flowing through the component. The increase in resistance is a measure of the temperature of the medium.

A measuring arrangement in which the component which heats the medium and measures the temperature in this region is metrologically coupled to the component which measures the temperature in that region of the medium which was not heated by the sensor proves to be favorable. This makes it possible to directly compensate for corruption caused by process-related temperature increases.

In one particularly advantageous variant of the invention, the evaluation unit emits a signal when a limit value of a particular degree of deposit formation is exceeded, in which case it proves to be particularly favorable for this signal to initiate a process which cleans the walls. The sensor signal can be processed and the cleaning process can be initiated using a process control system. As a result, the operators of the production installations no longer have to depend on empirical values but rather have reliable measurement data which are continuously detected. Operating costs are therefore reduced since the cleaning process is initiated only when a particular degree of deposit formation has been exceeded. Furthermore, the product quality is prevented from being adversely affected by the formation of deposits because the process has been running for too long without cleaning.

The duration of the cleaning operation can also be optimized by using the device according to the invention. The degree of deposit formation is continuously measured during the cleaning process. The deposit decreases as cleaning progresses. The cleaning operation is carried out until the deposit has been completely removed or undershoots a predefined limit value. This prevents the cleaning operation from being carried out for an unnecessarily long time and prevents both cleaning agents and production time from being wasted. Conversely, it is ensured that the cleaning operation is ended only when the pipelines are substantially free of deposits. This ensures a high degree of product quality.

One particular advantage of the invention is that the sensor can be used not only to determine the formation of deposits but simultaneously to measure the flow. According to the invention, this is a device which integratively combines two measuring methods in one device. The sensor may likewise be used to measure the flow velocity and to measure the temperature.

BRIEF DESCRIPTION OF THE DRAWINGS

The invention will be described in further detail hereinafter with reference to illustrative embodiments shown in the accompanying drawing figures in which.

DETAILED DESCRIPTION OF ILLUSTRATIVE EMBODIMENTS

Figure 1:
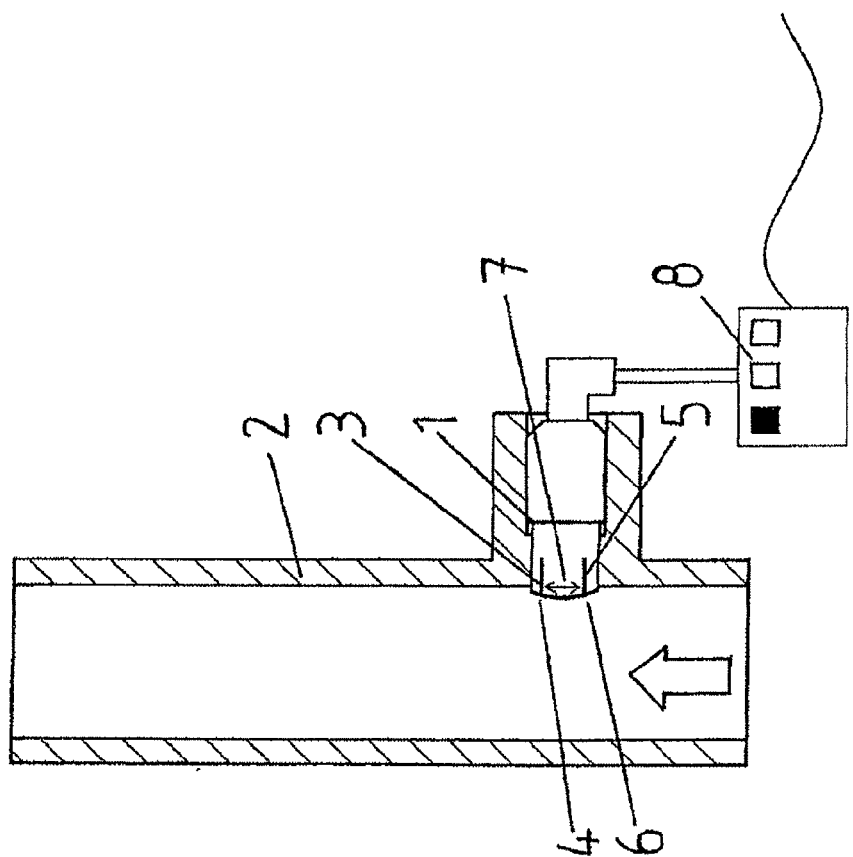
FIG. 1 is an illustration of a device according to the invention in a piece of pipe without a deposit.

FIG. 1 illustrates a sensor 1 which is integrated in a wall 2 of a pipe. A medium flows through the pipe. The sensor 1 comprises a component 3 which is heated and emits its heat to the medium. The component 3 is a temperature-dependent resistor which is in the form of a pin. The tip of the component 3 projects into the medium. A voltage is applied to the component 3, with the result that a current flows through the resistor and heats the component 3. The medium is locally heated in the region 4 around the tip of the component 3 at the location at which the component 3 is in contact with the medium. In the exemplary embodiment, the temperature of the medium at the location 4 is likewise measured by the component 3. The component 3 therefore has a dual function. It locally heats the medium and simultaneously measures the temperature in this region 4.

The sensor 1 comprises a second component 5 which measures the temperature of the medium at a location 6 which was not heated by the sensor 1. The component 5 is likewise a temperature-dependent resistor which is in the form of a pin and the tip of which projects into the medium. Measuring the temperature at a location 6 which was not heated by the sensor 1 makes it possible to cancel out effects which can be attributed to general heating of the medium on account of variable process conditions and are not based on heating by the sensor 1.

FIG. 1 illustrates a particularly advantageous embodiment of the invention in which the components 3 and 5 are arranged beside one another. The components 3 and 5 are in the form of pins which are beside one another in a parallel manner, both pins being arranged at a distance 7 from one another.

FIG. 1 shows the evaluation unit 8 to which the sensor 1 forwards its signals and with the aid of which the sensor 1 is controlled. The evaluation unit 8 is used as the power supply for the sensor.

Figure 2:
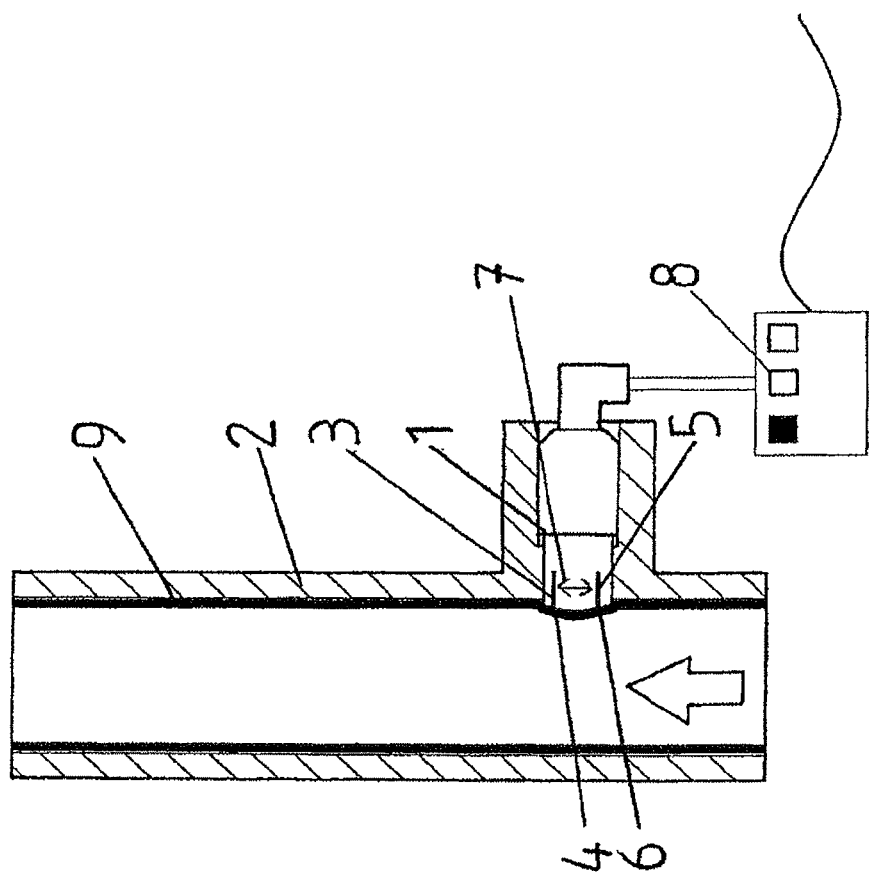
FIG. 2 is a schematic illustration of a device according to the invention in a piece of pipe with a deposit.

FIG. 2 differs from FIG. 1 only in that a deposit 9 has formed on the wall 2 of the pipeline. The component 3 of the sensor 1 is electrically heated. The component 3 is covered with a deposit 9 at the location at which the component 3 is in contact with the medium. The deposit 9 has an insulating effect. It shields the flow of the medium around the tip of the component 3. A higher temperature level is established in the region 4 on account of the insulating effect of the deposit 9. The period needed to establish a constant temperature level also differs from the measurements without a deposit 9.

The evaluation unit 8 determines the degree of deposit formation on the sensor by comparing the test measurement data with the formation of deposits with the measurement data without the formation of deposits which are used as reference data. The degree of deposit formation on the sensor can be used as measure of the degree of deposit formation on the walls 2 of the pipeline.

Figure 3A:
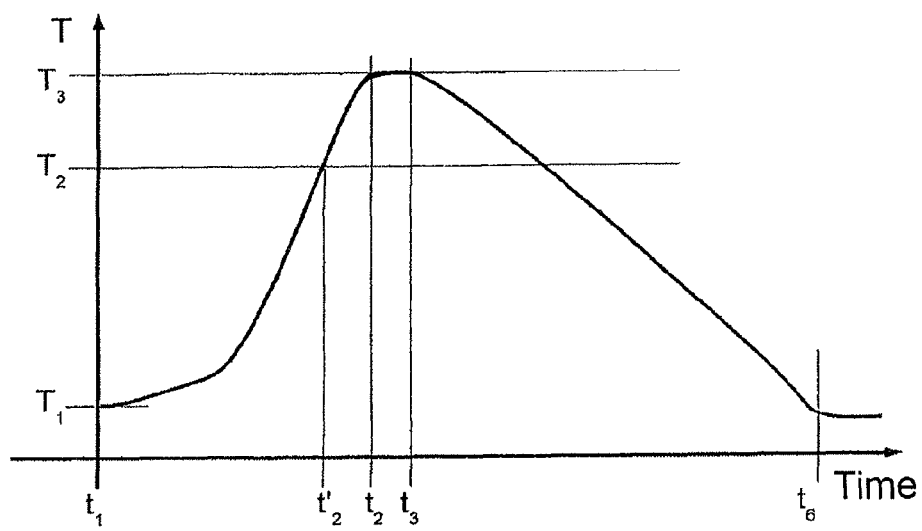
FIG. 3a is a temperature/time graph with a deposit.
Figure 3B:
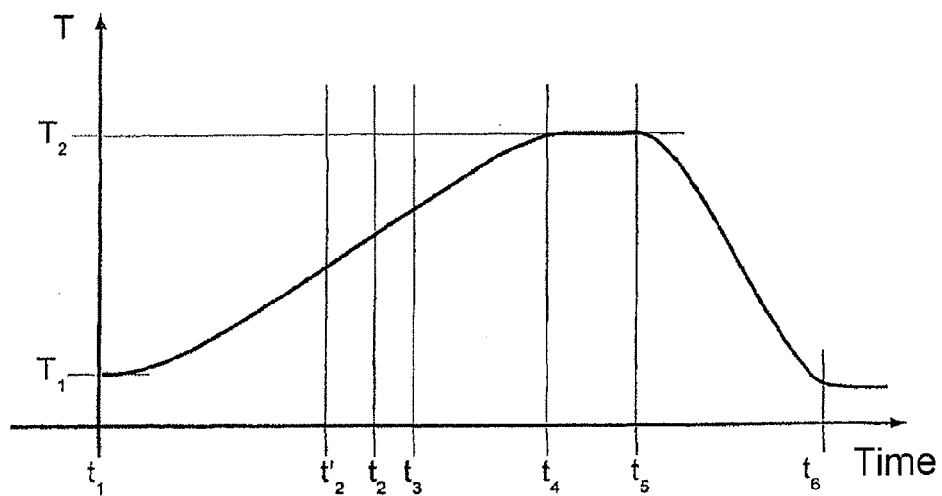
FIG. 3b is a temperature/time graph without a deposit.

FIGS. 3a and 3b illustrate the profile of the temperature measured with the component 3 in the region 4 of the medium as a function of time. FIG. 3a shows the profile with a deposit. FIG. 3b shows the profile without a deposit. At a time $t_1$, a voltage is suddenly applied to the component 3 of the sensor 1. The voltage is disconnected at particular times, $t_5$ during operation without a deposit and $t_3$ during operation with a deposit. It proves to be particularly favorable to repeat the connection and disconnection of the voltage in regular cycles. The measurement data are acquired during each cycle in this pulsed operation. It proves to be advantageous to calculate with the average values of the measurement data from a plurality of cycles during evaluation.

The component 3 is a temperature-dependent resistor. As soon as electrical current flows through the component 3, the component 3 heats up. The graphs 3a and 3b show the profiles of the temperature in the region 4 of the medium which is directly around the tip of the component 3.

FIG. 3b shows that, in the case of a sensor which is free of deposits, a period $t_4$-$t_1$ is needed to establish a constant temperature level $T_2$. The temperature increases from the temperature $T_1$ of the medium to a value $T_2$ during this phase. At a time $t_5$, the voltage across the component 3 is disconnected. The temperature decreases until it reaches a constant temperature level $T_1$ again at a time $t_6$.

FIG. 3a shows that, in the case of a sensor with a deposit, a period $t_2$-$t_1$ is needed to establish a constant temperature level $T_3$. The temperature level $T_3$ during a measurement with a deposit is above the temperature level $T_2$ without a deposit. The period $t_2$-$t_1$ which is needed to establish a constant temperature during a measurement with a deposit is shorter than the period $t_4$-$t_1$ without a deposit. The voltage across the component 3 is disconnected at a time $t_3$. The temperature decreases until it reaches a constant temperature level $T_1$ again at a time $t_6$. The period $t_6$-$t_3$ which is needed to establish a constant temperature during a measurement with a deposit is considerably longer than the period $t_6$-$t_5$ without a deposit.

The evaluation unit 8 can determine the degree of deposit formation in different ways.

One possibility is to compare the periods needed for cooling, the period $t_6$-$t_3$ with a deposit differing from the period $t_6$-$t_5$ without a deposit all the more, the more advanced the deposit formation.

A second possibility is to compare the periods needed for heating, the period $t_2$-$t_1$ with a deposit differing from the period $t_4$-$t_1$ without a deposit all the more, the more advanced the deposit formation.

A third possibility is to compare the periods needed for heating to the temperature $T_2$ which is established as a constant level during a measurement without a deposit, the period $t_2'$-$t_1$ with a deposit differing from the period $t_4$-$t_1$ without a deposit all the more, the more advanced the deposit formation.

A fourth possibility is to compare the temperature levels which are established after the component 3 has been heated, the temperature level $T_3$ with a deposit differing from the temperature level $T_2$ without a deposit all the more, the more advanced the deposit formation.

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations falling within the scope of the appended claims and equivalents thereof.

The invention claimed is:

1. A device for detecting the presence of deposits on a wall which is covered by a medium, said device comprising:
    a sensor integrated in or placed on the wall, said sensor including a heating element for heating the medium in an area surrounding the heating element, and said sensor detecting a temperature of said medium in the heated area or a temperature of the heating element; and
    an evaluation unit operatively connected to said sensor for receiving detected temperature signals from said sensor; said evaluation unit determining a degree of deposit formation on the wall by comparing received temperature signals with predetermined reference temperature data,
    wherein
        the heating element of the sensor locally heats the medium during a test measurement in which the detected temperature signals are generated to a temperature corresponding to a temperature generated in a reference measurement in which the predetermined reference temperature data is generated, and
        the evaluation unit determines the degree of deposit formation based on a difference in heating intensity required to attain the temperature in the test measurement and the temperature generated in the reference measurement.

2. The device as claimed in claim 1, wherein:
    a heating intensity with which the heating element is heated during a test measurement in which the detected temperature signals are generated corresponds to a heating intensity with which the heating element is heated during a reference measurement in which the predetermined reference temperature data is generated, and
    the evaluation unit determines the degree of deposit formation from a difference between a period, obtained from the test measurement, for a predetermined temperature response during at least one of heating by the heating element and cooling after heating by the heating element, and a period, obtained from the reference measurement, for the predetermined temperature response during at least one of heating by the heating element and cooling after heating by the heating element.

3. A device for detecting the presence of deposits on a wall which is covered by a medium, said device comprising:
    a sensor integrated in or placed on the wall, said sensor including a heating element for heating the medium in an area surrounding the heating element, and said sensor detecting a temperature of said medium in the heated area or a temperature of the heating element; and
    an evaluation unit operatively connected to said sensor for receiving detected temperature signals from said sensor; said evaluation unit determining a degree of deposit formation on the wall by comparing received temperature signals with predetermined reference temperature data, wherein
    a heating intensity with which the heating element is heated during a test measurement in which the detected temperature signals are generated corresponds to a heating intensity with which the heating element is heated during a reference measurement in which the predetermined reference temperature data is generated, and
    the evaluation unit determines the degree of deposit formation from a difference between a temperature established during the test measurement and a temperature established during the reference measurement.

4. The device as claimed in claim 1, wherein a single component is used both to locally heat the medium and to detect the temperature in the heated area.

5. The device as claimed in claim 4, wherein said single component comprises a temperature-dependent resistor.

6. The device as claimed in claim 1, further comprising second sensor for sensing a temperature of the medium at a location not heated by the heating element of the sensor.

7. The device as claimed in claim 6, wherein the second sensor for sensing the temperature at a location not heated by the heating element comprises a temperature-dependent resistor.

8. The device as claimed in claim 1, wherein the evaluation unit emits a detectable signal when a limit value for the degree of deposit formation is exceeded.

9. The device as claimed in claim 8, wherein the emitted detectable signal initiates a process which cleans the wall.

10. The device as claimed in claim 1, wherein, in addition to determining the degree of deposit formation, the sensor senses at least one additional parameter selected from the group consisting of flow of a medium flowing along the wall, the temperature of a medium flowing along the wall, and the flow velocity of a medium flowing along the wall.

11. A method for detecting the presence of a deposit on a wall which is covered by a medium, said method comprising:
    locally heating an area of the medium;
    sensing a temperature of the medium in the heated area or of a heating element used to heat the medium in the heated area; and
    determining a degree of deposit formation by comparing sensed temperature data from the heated area to predetermined reference temperature data;
    wherein
        the heating of the medium and the sensing of the temperature are effected by a sensor integrated in or placed on the wall in the area which is heated;
        the determination of the degree of deposit formation is effected by an evaluation unit operatively connected to receive signals from said sensor,
        the medium is heated during a test measurement in which the temperature of the medium is sensed to a temperature which corresponds to a temperature generated in a reference measurement in which the predetermined reference temperature data is generated, and
        the evaluation unit determines the degree of deposit formation based on a difference in heating intensity required to attain the temperature in the test measurement and the temperature generated in the reference measurement.

12. The method as claimed in claim 11, wherein:
    a heating intensity with which the medium is heated during a test measurement in which the temperature of the medium is sensed corresponds a heating intensity with which the heating element is heated during a reference measurement in which the predetermined reference temperature data is generated, and
    the evaluation unit determines the degree of deposit formation from a difference between a period, obtained from the test measurement, for a predetermined temperature response during at least one of heating by the heating element and cooling after heating by the heating element, and a period, obtained from the reference measurement, for the predetermined temperature response during at least one of heating by the heating element and cooling after heating by the heating element.

13. The method as claimed in claim 11, wherein a single component is used both to locally heat the medium and to detect the temperature in the heated area.

14. The method as claimed in claim 13, wherein said single component comprises a temperature-dependent resistor.

15. The method as claimed in claim 11, further comprising sensing the temperature of the medium at a location outside the heated area.

16. The method as claimed in claim 15, wherein the temperature of the medium at said location outside the heated area is sensed by a component comprising a temperature-dependent resistor.

17. The method as claimed in claim 11, wherein the evaluation unit emits a detectable signal when a limit value for the degree of deposit formation is exceeded.

18. The method as claimed in claim 17, wherein the emitted detectable signal initiates a process which cleans the wall.

19. The method as claimed in claim 11, wherein, in addition to determining the degree of deposit formation of deposits, the sensor senses at least one additional parameter selected from the group consisting of flow of a medium flowing along the wall, the temperature of a medium flowing along the wall, and the flow velocity of a medium flowing along the wall.

20. A method for detecting the presence of a deposit on a wall which is covered by a medium, said method comprising:
locally heating an area of the medium;
sensing a temperature of the medium in the heated area or of a heating element used to heat the medium in the heated area; and
determining a degree of deposit formation by comparing sensed temperature data from the heated area to predetermined reference temperature data;
wherein
the heating of the medium and the sensing of the temperature are effected by a sensor integrated in or placed on the wall in the area which is heated,
the determination of the degree of deposit formation is effected by an evaluation unit operatively connected to receive signals from said sensor,
a heating intensity with which the medium is heated during a test measurement in which the temperature of the medium is sensed corresponds a heating intensity with which the heating element is heated during a reference measurement in which the predetermined reference temperature data is generated, and
the evaluation unit determines the degree of deposit formation from difference between a temperature established during the test measurement and a temperature established during the reference measurement.

* * * * *